United States Patent
Farwick et al.

(10) Patent No.: US 7,129,066 B2
(45) Date of Patent: Oct. 31, 2006

(54) NUCLEOTIDE SEQUENCES CODING FOR THE CITE GENE

(75) Inventors: Mike Farwick, Bielefeld (DE); Klaus Huthmacher, Geinhausen (DE); Achim Marx, Bielefeld (DE); Brigitte Bathe, Salzkotten (DE); Walter Pfefferle, Halle (DE)

(73) Assignee: Degussa AG, Dusseldorf, DE (US)

( * ) Notice: Subject to any disclaimer, the term of this patent is extended or adjusted under 35 U.S.C. 154(b) by 463 days.

(21) Appl. No.: 10/375,355

(22) Filed: Feb. 28, 2003

(65) Prior Publication Data

US 2003/0157666 A1     Aug. 21, 2003

Related U.S. Application Data

(62) Division of application No. 09/770,688, filed on Jan. 29, 2001.

(51) Int. Cl.
| | |
|---|---|
| *C12P 13/08* | (2006.01) |
| *C12P 13/04* | (2006.01) |
| *C12N 9/88* | (2006.01) |
| *C07H 21/04* | (2006.01) |

(52) U.S. Cl. ............ 435/115; 435/106; 435/232; 536/23.2

(58) Field of Classification Search ........... 435/106, 435/115, 232, 252.3, 252.33, 440; 536/23.2
See application file for complete search history.

(56) References Cited

FOREIGN PATENT DOCUMENTS

| | | | |
|---|---|---|---|
| EP | 1 108 790 | | 6/2001 |
| JP | 56 88 799 | | 7/1981 |
| JP | 56-88799 | * | 7/1981 |
| WO | WO 01 00844 | | 1/2001 |

OTHER PUBLICATIONS

Kalinowski et al. (2003) Journal of Bacteriology, vol. 104, pp. 5-25.*
Jakoby et al., "AmtR, a global repressor in the nitrogen regulation system of *Corynebacterium glutamicum*", Molecular Biology, vol. 37, Nr. 4, p. 964-977 & Database EMBL, Accession No. AJ133719, XP002176655.
Database EMBL, Accession No. AX127145; AX114121, Nakagawa et al., "Sequence 7061 from patent EP1108790", 2001.
Database EMBL, Accession No. AX121047; Nakagawa et al., "Sequence 963 from patent EP1108790", 2001.
Database EMBL, Accession No. AX124547, Nakagawa et al., "Sequence 4463 from patent EP1108790", 2001.
Database EMBL, Accession No. AX121046, Nakagawa et al., "Sequence 962 from patent EP1108790", 2001.
Database EMBL, Accession No. AX121048, Nakagawa et al., "Sequence 964 from patent EP1108790", 2001.

* cited by examiner

*Primary Examiner*—Elizabeth Slobodyansky
(74) *Attorney, Agent, or Firm*—Pillsbury Winthrop Shaw Pittman LLP

(57) ABSTRACT

The invention relates to an isolated polynucleotide containing a polynucleotide sequence selected from the group
a) polynucleotide that is at least 70% identical with a polynucleotide that codes for a polypeptide containing the amino acid sequence of SEQ ID No. 2,
b) polynucleotide that codes for a polypeptide containing an amino acid sequence that is at least 70% identical with the amino acid sequence of SEQ ID No. 2,
c) polynucleotide that is complementary to the polynucleotides of a) or b), and
d) polynucleotide containing at least 15 consecutive nucleotides of the polynucleotide sequence of a), b) or c), and to a process for the production of L-amino acids by fermentation using coryneform bacteria in which at least the citE gene is present in attenuated form, and to the use of polynucleotides containing the sequences of the invention as hybridization probes.

6 Claims, 1 Drawing Sheet

Figure 1: Plasmid pCR2.1citEint
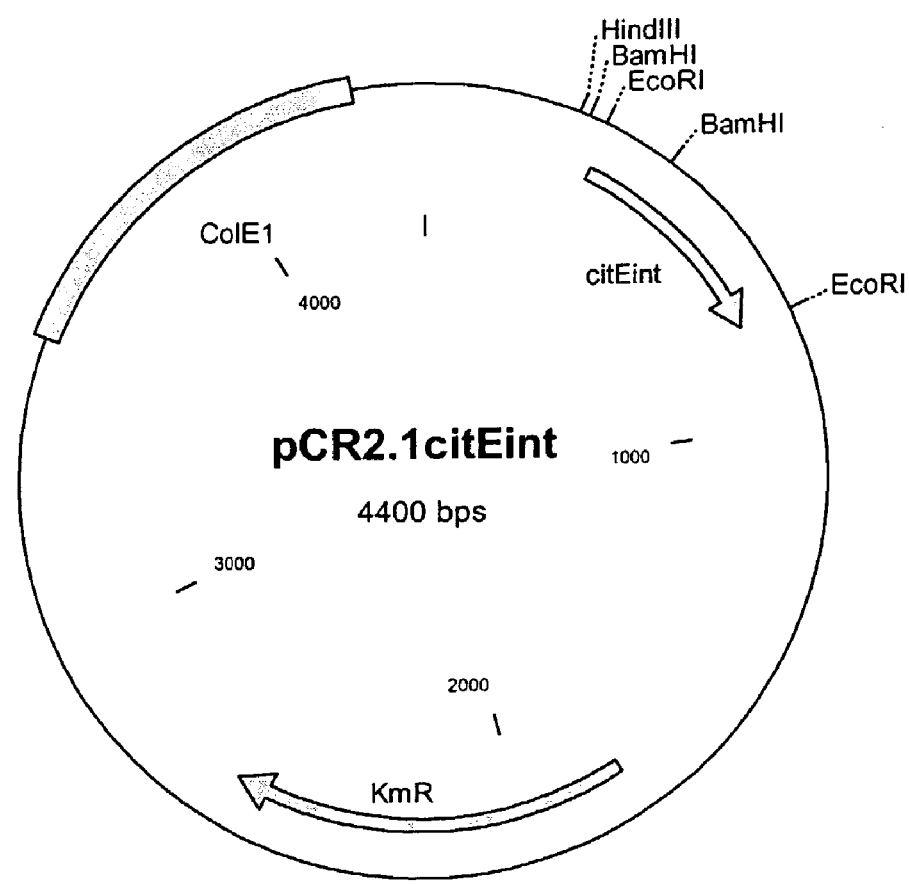

NUCLEOTIDE SEQUENCES CODING FOR THE CITE GENE

This is a divisional of U.S. patent application Ser. No. 09/770,688, filed Jan. 29, 2001.

The invention provides nucleotide sequences from coryneform bacteria coding for the citE gene, and a process for the production of amino acids by fermentation using bacteria in which the citE gene is attenuated.

PRIOR ART

L-amino acids, especially L-lysine, are used in human medicine and in the pharmaceuticals industry, in the foodstuffs industry and, very especially, in the feeding of animals.

It is known that amino acids are produced by fermentation of strains of coryneform bacteria, especially *Corynebacterium glutamicum*. Because of their great importance, attempts are continuously being made to improve the production processes. Improvements to the processes may concern measures relating to the fermentation, such as, for example, stirring and oxygen supply, or the composition of the nutrient media, such as, for example, the sugar concentration during the fermentation, or working up to the product form by, for example, ion-exchange chromatography, or the intrinsic performance properties of the microorganism itself.

In order to improve the performance properties of such microorganisms, methods of mutagenesis, selection and mutant selection are employed. Such methods yield strains which are resistant to antimetabolites or are auxotrophic for metabolites that are important in terms of regulation, and which produce amino acids.

For a number of years, methods of recombinant DNA technology have also been used for improving the strain of L-amino acid-producing strains of Corynebacterium, by amplifying individual amino acid biosynthesis genes and studying the effect on amino acid production.

OBJECT OF THE INVENTION

The inventors have set themselves the object of providing novel measures for the improved production of amino acids by fermentation.

DESCRIPTION OF THE INVENTION

Where L-amino acids or amino acids are mentioned hereinbelow, they are to be understood as meaning one or more amino acids, including their salts, selected from the group L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-lysine is especially preferred.

Where L-lysine or lysine is mentioned hereinbelow, it is to be understood as meaning not only the bases but also the salts, such as, for example, lysine monohydrochloride or lysine sulfate.

The invention provides an isolated polynucleotide from coryneform bacteria, containing a polynucleotide sequence coding for the citE gene, selected from the group a) polynucleotide that is at least 70% identical with a polynucleotide that codes for a polypeptide containing the amino acid sequence of SEQ ID No. 2, b) polynucleotide that codes for a polypeptide containing an amino acid sequence that is at least 70% identical with the amino acid sequence of SEQ ID No. 2, c) polynucleotide that is complementary to the polynucleotides of a) or b), d) polynucleotide containing at least 15 consecutive nucleotides of the polynucleotide sequence of a), b) or c), the polypeptide preferably exhibiting the activity of citrate lyase E.

The invention also provides the above-mentioned polynucleotide, it preferably being a replicatable DNA containing:

(i) the nucleotide sequence shown in SEQ ID No. 1, or
(ii) at least one sequence that corresponds to sequence (i) within the degeneracy of the genetic code, or
(iii) at least one sequence that hybridizes with the sequences that are complementary to sequences (i) or (ii), and optionally
(iv) sense mutations in (i) which are neutral in terms of function and which do not change the activity of the protein/polypeptide.

Finally, the invention also provides polynucleotides selected from the group a) polynucleotides containing at least 15 consecutive nucleotides selected from the nucleotide sequence of SEQ ID No. 1 between positions 1 and 601 b) polynucleotides containing at least 15 consecutive nucleotides selected from the nucleotide sequence of SEQ ID No. 1 between positions 602 and 1423 c) polynucleotides containing at least 15 consecutive nucleotides selected from the nucleotide sequence of SEQ ID No. 1 between positions 1424 and 1964.

The invention also provides
a replicatable polynucleotide, especially DNA, containing the nucleotide sequence as shown in SEQ ID No. 1;
a polynucleotide that codes for a polypeptide containing the amino acid sequence as shown in SEQ ID No. 2;
a vector containing parts of the polynucleotide according to the invention, but at least 15 consecutive nucleotides of the claimed sequence, and coryneform bacteria in which the citE gene is attenuated especially by an insertion or deletion.

The invention also provides polynucleotides consisting substantially of a polynucleotide sequence, which are obtainable by screening, by means of hybridization, a corresponding gene library of a coryneform bacteria that contains the complete gene or parts thereof, using a probe containing the sequence of the polynucleotide of the invention according to SEQ ID No. 1 or a fragment thereof, and isolating the mentioned polynucleotide sequence.

Polynucleotides that contain the sequences of the invention are suitable as hybridization probes for RNA, cDNA and DNA, in order to isolate in their complete length nucleic acids or polynucleotides or genes that code for citrate lyase E, or in order to isolate nucleic acids or polynucleotides or genes that are very similar to the sequence of the citE gene. They are likewise suitable for incorporation into so-called "arrays", "micro arrays" or "DNA chips" in order to detect and determine the corresponding polynucleotides.

Polynucleotides that contain the sequences of the invention are also suitable as primers, with the aid of which it is possible, by means of the polymerase chain reaction (PCR), to produce DNA of genes that code for citrate lyase E.

Such oligonucleotides acting as probes or primers contain at least 25, 26, 27, 28, 29 or 30, preferably at least 20, 21, 22, 23 or 24, very especially preferably at least 15, 16, 17, 18 or 19, consecutive nucleotides. Also suitable are oligonucleotides having a length of at least 31, 32, 33, 34, 35, 36, 37, 38, 39 or 40 or of at least 41, 42, 43, 44, 45, 46, 47, 48, 49 or 50 nucleotides. Oligonucleotides having a length of at least 100, 150, 200, 250 or 300 nucleotides may also be suitable.

"Isolated" means removed from its natural environment.

"Polynucleotide" generally refers to polyribonucleotides and polydeoxyribonucleotides, it being possible for the RNA or DNA to be unmodified or modified.

The polynucleotides of the invention include a polynucleotide according to SEQ ID No. 1 or a fragment prepared therefrom, and also polynucleotides that are at least from 70% to 80%, preferably at least from 81% to 85%, especially at least from 86% to 90%, and very especially at least 91%, 93%, 95%, 97% or 99%, identical with the polynucleotide according to SEQ ID No. 1, or with a fragment prepared therefrom.

"Polypeptides" are to be understood as being peptides or proteins that contain two or more amino acids bonded via peptide bonds.

The polypeptides of the invention include a polypeptide according to SEQ ID No. 2, especially those having the biological activity of citrate lyase E, and also those that are at least from 70% to 80%, preferably at least from 81% to 85%, especially at least from 86% to 90%, and very especially at least 91%, 93%, 95%, 97% or 99%, identical with the polypeptide according to SEQ ID No. 2 and exhibit the mentioned activity.

The invention also provides a process for the production, by fermentation, of amino acids selected from the group L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine, using coryneform bacteria which, in particular, already produce amino acids and in which the nucleotide sequences coding for the citE gene are attenuated, especially excluded or expressed at a low level.

The term "attenuation" in this connection describes the diminution or exclusion of the intracellular activity of one or more enzymes or proteins in a microorganism that are coded for by the corresponding DNA, by, for example, using a weak promoter or using a gene or allele that codes for a corresponding enzyme or protein having low activity, or by inactivating the corresponding gene or enzyme (protein), and optionally by combining those measures.

The microorganisms provided by the present invention may produce amino acids from glucose, saccharose, lactose, fructose, maltose, molasses, starch, cellulose or from glycerol and ethanol. They may be representatives of coryneform bacteria, especially of the genus Corynebacterium. In the case of the genus Corynebacterium, special mention may be made of the species *Corynebacterium glutamicum*, which is known to those skilled in the art for its ability to produce L-amino acids.

Suitable strains of the genus Corynebacterium, especially of the species *Corynebacterium glutamicum* (*C. glutamicum*), are especially the known wild type strains

*Corynebacterium glutamicum* ATCC13032
*Corynebacterium acetoglutamicum* ATCC15806
*Corynebacterium acetoacidophilum* ATCC13870
*Corynebacterium melassecola* ATCC17965
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020 and L-amino acid-producing mutants or strains prepared therefrom, such as, for example, the L-lysine-producing strains

*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464
*Corynebacterium glutamicum* DM58-1
*Corynebacterium glutamicum* DG52-5
*Corynebacterium glutamicum* DSM5715 and
*Corynebacterium glutamicum* DSM12866.

The new citE gene of *C. glutamicum* coding for the enzyme citrate lyase E (EC No. 4.1.3.6) has been isolated.

In order to isolate the citE gene or other genes from *C. glutamicum*, a gene library of that microorganism in *Escherichia coli* (*E. coli*) is first prepared. The preparation of gene libraries is described in generally known textbooks and handbooks. There may be mentioned as an example the textbook of Winnacker: Gene und Klone, Eine Einführung in die Gentechnologie (Verlag Chemie, Weinheim, Germany, 1990) or the handbook of Sambrook et al.: Molecular Cloning, A Laboratory Manual (Cold Spring Harbor Laboratory Press, 1989). A very well known gene library is that of the *E. coli* K-12 strain W3110, which has been prepared by Kohara et al. (Cell 50, 495–508 (1987)) in λ-vectors. Bathe et al. (Molecular and General Genetics, 252:255–265, 1996) describe a gene library of *C. glutamicum* ATCC13032, which has been prepared with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575).

Börmann et al. (Molecular Microbiology 6(3), 317–326 (1992)) in turn describe a gene library of *C. glutamicum* ATCC13032 using the cosmid pHC79 (Hohn and Collins, 1980, Gene 11, 291–298).

For the preparation of a gene library of *C. glutamicum* in *E. coli* it is also possible to use plasmids such as pBR322 (Bolivar, 1979, Life Sciences, 25, 807–818) or pUC9 (Vieira et al., 1982, Gene, 19:259–268). Suitable hosts are especially those *E. coli* strains that are restriction- and recombination-defective, such as, for example, strain DH5αmcr, which has been described by Grant et al. (Proceedings of the National Academy of Sciences USA, 87 (1990) 4645–4649). The long DNA fragments cloned with the aid of cosmids or other λ-vectors can then in turn be subcloned into customary vectors suitable for DNA sequencing and then sequenced, as is described, for example, in Sanger et al. (Proceedings of the National Academy of Sciences of the United States of America, 74:5463–5467, 1977).

The resulting DNA sequences can then be studied using known algorithms or sequence-analysis programs, such as, for example, that of Staden (Nucleic Acids Research 14, 217–232 (1986)), that of Marck (Nucleic Acids Research 16, 1829–1836(1988)) or the GCG program of Butler (Methods of Biochemical Analysis 39, 74–97 (1998)).

The novel DNA sequence of *C. glutamicum* coding for the citE gene has been found and, as SEQ ID No. 1, forms part of the present invention. Furthermore, the amino acid sequence of the corresponding protein has been derived from the present DNA sequence using the methods described above. The resulting amino acid sequence of the citE gene product is shown in SEQ ID No. 2. It is known that enzymes belonging to the host are able to cleave the N-terminal amino acid methionine or formylmethionine of the protein that is formed.

Coding DNA sequences that result from SEQ ID No. 1 by the degeneracy of the genetic code also form part of the invention. Likewise, DNA sequences that hybridize with SEQ ID No. 1 or parts of SEQ ID No. 1 form part of the invention. Furthermore, to those skilled in the art, conservative amino acid substitutions, such as, for example, the substitution of glycine with alanine or of aspartic acid with glutamic acid, in proteins are known as sense mutations, which do not lead to any fundamental change in the activity of the protein, that is to say are neutral in terms of function. Such mutations are known inter alia also as neutral substitutions. It is also known that changes at the N- and/or C-terminus of a protein do not substantially impair its function or may even stabilise it. The person skilled in the art will find relevant information inter alia in Ben-Bassat et al. (Journal of Bacteriology 169:751–757(1987)), in O'Regan et al. (Gene 77:237–251(1989)), in Sahin-Toth et al. (Protein Sciences 3:240–247(1994)), in Hochuli et al. (Bio/Technology 6:1321–1325(1988)) and in known textbooks of genetics and molecular biology. Amino acid sequences that result in a corresponding manner from SEQ ID No. 2 likewise form part of the invention.

Similarly, DNA sequences that hybridize with SEQ ID No. 1 or parts of SEQ ID No. 1 form part of the invention. Finally, DNA sequences that are produced by polymerase chain reaction (PCR) using primers that result from SEQ ID No. 1 form part of the invention. Such oligonucleotides typically have a length of at least 15 nucleotides.

The person skilled in the art will find instructions on the identification of DNA sequences by means of hybridization inter alia in the handbook "The DIG System Users Guide for Filter Hybridization" from Boehringer Mannheim GmbH (Mannheim, Germany, 1993) and in Liebl et al. (International Journal of Systematic Bacteriology 41: 255–260 (1991)). The hybridization takes place under stringent conditions, that is to say there are formed only hybrids in which the probe and the target sequence, i.e. the polynucleotides treated with the probe, are at least 70% identical. It is known that the stringency of the hybridization, including the washing steps, is influenced or determined by varying the buffer composition, the temperature and the salt concentration. The hybridization reaction is preferably carried out with relatively low stringency as compared with the washing steps (Hybaid Hybridisation Guide, Hybaid Limited, Teddington, UK, 1996).

There may be used for the hybridization reaction, for example, a 5×SSC buffer at a temperature of approximately from 50° C. to 68° C. In that case, probes may also hybridize with polynucleotides that are less than 70% identical with the sequence of the probe. Such hybrids are less stable and are removed by washing under stringent conditions. That may be achieved, for example, by lowering the salt concentration to 2×SSC and optionally subsequently to 0.5×SSC (The DIG System User's Guide for Filter Hybridisation, Boehringer Mannheim, Mannheim, Germany, 1995), a temperature of approximately from 50° C. to 68° C. being set. It is optionally possible to lower the salt concentration down to 0.1×SSC. By raising the hybridization temperature stepwise from 50° C. to 68° C. in steps of approximately from 1 to 2° C., it is possible to isolate polynucleotide fragments that are, for example, at least 70% or at least 80% or at least from 90% to 95% or at least from 96% to 99% identical with the sequence of the probe used. It is likewise possible to isolate polynucleotide fragments that are completely identical with the sequence of the probe used. Further instructions for hybridization are commercially available in the form of so-called kits (e.g. DIG Easy Hyb from Roche Diagnostics GmbH, Mannheim, Germany, Catalog No. 1603558).

The person skilled in the art will find instructions on the amplification of DNA sequences with the aid of the polymerase chain reaction (PCR) inter alia in the handbook of Gait: Oligonukleotide (sic) synthesis: A Practical Approach (IRL Press, Oxford, UK, 1984) and in Newton and Graham: PCR (Spektrum Akademischer Verlag, Heidelberg, Germany, 1994).

It has been found that coryneform bacteria produce amino acids in an improved manner after attenuation of the citE gene.

In order to achieve attenuation, either the expression of the citE gene or the catalytic/regulatory properties of the enzyme protein can be diminished or excluded. The two measures may optionally be combined.

A diminution of gene expression can be effected by carrying out the culturing in a suitable manner or by genetic alteration (mutation) of the signal structures of gene expression. Signal structures of gene expression are, for example, repressor genes, activator genes, operators, promoters, attenuators, ribosome-binding sites, the start codon and terminators. The person skilled in the art will find information thereon, for example, in patent application WO 96/15246, in Boyd and Murphy (Journal of Bacteriology 170: 5949 (1988)), in Voskuil and Chambliss (Nucleic Acids Research 26: 3548 (1998), in Jensen and Hammer (Biotechnology and Bioengineering 58: 191 (1998)), in Pátek et al. (Microbiology 142: 1297 (1996)), Vasicova et al. (Journal of Bacteriology 181: 6188 (1999)) and in known textbooks of genetics and molecular biology, such as, for example, the textbook of Knippers ("Molekulare Genetik", 6th edition, Georg Thieme Verlag, Stuttgart, Germany, 1995) or that of Winnacker ("Gene und Klone", VCH Verlagsgesellschaft, Weinheim, Germany, 1990).

Mutations that lead to a change in or diminution of the catalytic properties of enzyme proteins are known from the prior art; examples which may be mentioned are the works of Qiu and Goodman (Journal of Biological Chemistry 272: 8611–8617(1997)), Sugimoto et al. (Bioscience Biotechnology and Biochemistry 61: 1760–1762(1997)) and Möckel ("Die Threonindehydratase aus *Corynebacterium glutamicum*: Aufhebung der allosterischen Regulation und Struktur des Enzyms", Berichte des Forschungszentrums Jülichs, Jül-2906, ISSN09442952, Jülich, Germany, 1994). Summaries are to be found in known textbooks of genetics and molecular biology, such as, for example, that of Hagemann ("Allgemeine Genetik", Gustav Fischer Verlag, Stuttgart, 1986).

There come into consideration as mutations transitions, transversions, insertions and deletions. In dependence on the effect of the amino acid substitution on the enzyme activity, missense mutations or nonsense mutations are referred to. Insertions or deletions of at least one base pair (bp) in a gene lead to frame shift mutations, as a result of which incorrect amino acids are incorporated or the translation breaks off prematurely. Deletions of several codons typically lead to complete loss of enzyme activity. Instructions for the production of such mutations are part of the prior art and will be found in known textbooks of genetic and molecular biology, such as, for example, the textbook of Knippers ("Molekulare Genetik", 6th edition, Georg Thieme Verlag, Stuttgart, Germany, 1995), that of Winnacker ("Gene und Klone", VCH Verlagsgesellschaft, Weinheim, Germany, 1990) or that of Hagemann ("Allgemeine Genetik", Gustav Fischer Verlag, Stuttgart, 1986).

A common method of mutating genes of *C. glutamicum* is the method of gene disruption and of gene replacement described by Schwarzer and Puhler (Bio/Technology 9, 84–87 (1991)).

In the method of gene disruption, a central portion of the coding region of the gene in question is cloned into a plasmid vector which is able to replicate in a host (typically *E. coli*), but not in *C. glutamicum*. Suitable vectors are, for example, pSUP301 (Simon et al., Bio/Technology 1, 784–791 (1983)), pK18mob or pK19mob (Schäfer et al., Gene 145, 69–73 (1994)), pK18mobsacB or pK19mobsacB (Jäger et al., Journal of Bacteriology 174: 5462–5465 (1992)), pGEM-T (Promega corporation, Madison, Wis., USA), pCR2.1-TOPO (Shuman (1994). Journal of Biological Chemistry 269:32678–32684; U.S. Pat. No. 5,487,993), pCR®Blunt (Invitrogen, Groningen, Netherlands; Bernard et al., Journal of Molecular Biology, 234: 534–541(1993)) or pEM1 (Schrumpf et al., 1991, Journal of Bacteriology 173:4510–4516). The plasmid vector containing the central portion of the coding region of the gene is then transferred to the desired strain of *C. glutamicum* by conjugation or transformation. The method of conjugation is described, for example, in Schäfer et al. (Applied and Environmental Microbiology 60, 756–759(1994)). Methods of transformation are described, for example, in Thierbach et al. (Applied Microbiology and Biotechnology 29, 356–362(1988)), Dunican and Shivnan (Bio/Technology 7, 1067–1070 (1989)) and Tauch et al. (FEMS Microbiological Letters 123, 343–347 (1994)). After homologous recombination by means of a cross-over occurrence, the coding region of the gene in question is interrupted by the vector sequence, and two incomplete alleles lacking the 3'- and the 5'-end, respectively, are obtained. That method has been used, for example, by Fitzpatrick et al. (Applied Microbiology and Biotechnology 42, 575–580 (1994)) to exclude the recA gene of *C. glutamicum*.

In the gene replacement method, a mutation, such as, for example, a deletion, insertion or base substitution, is produced in vitro in the gene in question. The allele that is produced is in turn cloned into a vector that is not replicative for *C. glutamicum*, and the latter is then transferred to the desired host of *C. glutamicum* by transformation or conjugation. After homologous recombination by means of a first cross-over occurrence effecting integration and by means of a suitable second cross-over occurrence effecting an excision in the target gene or in the target sequence, incorporation of the mutation or of the allele is achieved. That method has been used, for example, by Peters-Wendisch et al. (Microbiology 144, 915–927 (1998)) to exclude the pyc gene of *C. glutamicum* by means of a deletion.

A deletion, insertion or a base substitution may thus be incorporated into the citE gene.

In addition, it may be advantageous for the production of L-amino acids, in addition to attenuating the citE gene, to enhance, especially to overexpress, one or more enzymes of the biosynthesis pathway in question, of glycolysis, of the anaplerotic pathway, of the citric acid cycle, of the pentose phosphate cycle, of amino acid export, and, optionally, regulatory proteins.

The term "enhancement" in this connection describes an increase in the intracellular activity of one or more enzymes (proteins) in a microorganism that are coded for by the corresponding DNA, by, for example, increasing the number of copies of the gene or genes, using a strong promoter or using a gene or allele that codes for a corresponding enzyme (protein) having high activity, and optionally by combining those measures.

Accordingly, for the production of L-lysine, in addition to attenuating the citE gene, one or more genes selected from the group the gene dapA coding for dihydrodipicolinate synthase (EP-B 0 197 335), the gene gap coding for glyceraldehyde 3-phosphate dehydrogenase (Eikmanns (1992), Journal of Bacteriology 174:6076–6086), the gene tpi coding for triose phosphate isomerase (Eikmanns (1992), Journal of Bacteriology 174:6076–6086), the gene pgk coding for 3-phosphoglycerate kinase (Eikmanns (1992), Journal of Bacteriology 174:6076–6086), the gene zwf coding for glucose-6-phosphate dehydrogenase (JP-A-09224661), the gene pyc coding for pyruvate carboxylase (DE-A-198 31 609), the gene mqo coding for malate quinone oxidoreductase (Molenaar et al., European Journal of Biochemistry 254, 395–403 (1998)), the gene lysC coding for a feed-back resistant aspartate kinase (Accession No. P26512; EP-B-0387527; EP-A-0699759; WO 00/63388), the gene lysE coding for lysine export (DE-A-195 48 222), the gene zwa1 coding for the Zwa1 protein (DE: 19959328.0, DSM 13115)

may at the same time be enhanced, especially overexpressed.

Furthermore, it may be advantageous for the production of L-lysine, in addition to attenuating the citE gene, at the same time to attenuate, especially to diminish the expression of, one or more genes selected from the group the gene pck coding for phosphoenol pyruvate carboxykinase (DE 199 50 409.1, DSM 13047), the gene pgi coding for glucose-6-phosphate isomerase (U.S. Ser. No. 09/396,478, DSM 12969), the gene poxB coding for pyruvate oxidase (DE:1995 1975.7, DSM 13114), the gene zwa2 coding for the Zwa2 protein (DE: 19959327.2, DSM 13113), the gene hom coding for homoserine dehydrogenase (EP-A-0131171), the gene thrB coding for homoserine kinase (Peoples, O. W., et al., Molecular Microbiology 2 (1988): 63–72), and the gene panD coding for aspartate decarboxylase (EP-A-1006192).

Attenuation of homoserine dehydrogenase can be achieved, inter alia, also by amino acid substitution, such as, for example, by substituting L-valine with L-alanine, L-glycine or L-leucine at position 59 of the enzyme protein, by substituting L-valine with L-isoleucine, L-valine or L-leucine at position 104 of the enzyme protein, and/or by substituting L-asparagine with L-threonine or L-serine at position 118 of the enzyme protein.

Attenuation of homoserine kinase can be achieved, inter alia, also by amino acid substitution, such as, for example, by substituting L-alanine with L-valine, L-glycine or L-leucine at position 133 of the enzyme protein, and/or by substituting L-proline with L-threonine, L-isoleucine or L-serine at position 138 of the enzyme protein.

Attenuation of aspartate decarboxylase can be achieved, inter alia, also by amino acid substitution, such as, for example, by substituting L-alanine with L-glycine, L-valine or L-isoleucine at position 36 of the enzyme protein.

It may also be advantageous for the production of amino acids, in addition to attenuating the citE gene, to exclude undesired secondary reactions (Nakayama: "Breeding of Amino Acid Producing Microorganisms", in: Overproduction of Microbial Products, Krumphanzl, Sikyta, Vanek (eds.), Academic Press, London, UK, 1982).

The microorganisms produced according to the invention also form part of the invention and can be cultivated, for the purposes of the production of L-amino acids, continuously or discontinuously in the batch, fed batch or repeated fed batch process. A summary of known cultivation methods is described in the textbook of Chmiel (Bioprozesstechnik 1. Einführung in die Bioverfahrenstechnik (Gustav Fischer Verlag, Stuttgart, 1991)) or in the textbook of Storhas (Bioreaktoren und periphere Einrichtungen (Vieweg Verlag, Braunschweig/Wiesbaden, 1994)).

The culture medium to be used must meet the requirements of the strains in question in a suitable manner. Descriptions of culture media for various microorganisms are to be found in the handbook "Manual of Methods for General Bacteriology" of the American Society for Bacteriology (Washington D.C., USA, 1981).

There may be used as the carbon source sugars and carbohydrates, such as, for example, glucose, saccharose, lactose, fructose, maltose, molasses, starch and cellulose, oils and fats, such as, for example, soybean oil, sunflower oil, groundnut oil and coconut oil, fatty acids, such as, for example, palmitic acid, stearic acid and linoleic acid, alcohols, such as, for example, glycerol and ethanol, and organic acids, such as, for example, acetic acid. Those substances may be used individually or in the form of a mixture.

There may be used as the nitrogen source organic nitrogen-containing compounds, such as peptones, yeast extract, meat extract, malt extract, corn steep liquor, soybean flour and urea, or inorganic compounds, such as ammonium sulfate, ammonium chloride, ammonium phosphate, ammonium carbonate and ammonium nitrate. The nitrogen sources may be used individually or in the form of a mixture.

There may be used as the phosphorus source phosphoric acid, potassium dihydrogen phosphate or dipotassium hydrogen phosphate or the corresponding sodium-containing salts. The culture medium must also contain salts of metals, such as, for example, magnesium sulfate or iron sulfate, which are necessary for growth. Finally, essential growth substances, such as amino acids and vitamins, may be used in addition to the above-mentioned substances. Suitable precursors may also be added to the culture medium. The mentioned substances may be added to the culture in the form of a single batch, or they may be fed in in a suitable manner during the cultivation.

In order to control the pH value of the culture, basic compounds, such as sodium hydroxide, potassium hydroxide, ammonia or ammonia water, or acid compounds, such as phosphoric acid or sulfuric acid, are expediently used. In order to control the development of foam, anti-foams, such as, for example, fatty acid polyglycol esters, may be used. In order to maintain the stability of plasmids, suitable substances having a selective action, such as, for example, antibiotics, may be added to the medium. In order to maintain aerobic conditions, oxygen or gas mixtures containing oxygen, such as, for example, air, are introduced into the culture. The temperature of the culture is normally from 20° C. to 45° C. and preferably from 25° C. to 40° C. The culture is continued until the maximum amount of the desired product has formed. That aim is normally achieved within a period of from 10 hours to 160 hours.

Methods of determining L-amino acids are known from the prior art. The analysis may be carried out, for example, as described in Spackman et al. (Analytical Chemistry, 30, (1958), 1190) by anion-exchange chromatography with subsequent ninhydrin derivatization, or it may be carried out by reversed phase HPLC, as described in Lindroth et al. (Analytical Chemistry (1979) 51: 1167–1174).

A pure culture of *Escherichia coli* strain Top 10/pCR2.1citEint was deposited on 12 Jan. 2001 at the Deutsche Sammlung für Mikroorganismen und Zellkulturen (DSMZ, Braunschweig, Germany) as DSM13981 in accordance with the Budapest Treaty.

The process of the invention is used for the production of amino acids, especially L-lysine, by fermentation.

The present invention is explained in greater detail below by means of Examples.

The isolation of plasmid DNA from *Escherichia coli* and all techniques for restriction, Klenow and alkaline phosphatase treatment were carried out according to Sambrook et al. (Molecular Cloning. A Laboratory Manual, 1989, Cold Spring Harbour Laboratory Press, Cold Spring Harbor, N.Y., USA). Methods for the transformation of *Escherichia coli* are also described in that handbook.

The composition of common nutrient media, such as LB or TY medium, will also be found in the handbook of Sambrook et al.

EXAMPLE 1

Preparation of a Genomic Cosmid Gene Library from *C. glutamicum* ATCC 13032

Chromosomal DNA from *C. glutamicum* ATCC 13032 is isolated as described in Tauch et al. (1995, Plasmid 33:168–179) and partially cleaved with the restriction enzyme Sau3AI (Amersham Pharmacia, Freiburg, Germany, product description Sau3AI, Code no. 27-0913-02). The DNA fragments are dephosphorylated with shrimp alkaline phosphatase (Roche Molecular Biochemicals, Mannheim, Germany, product description SAP, Code no. 1758250). The DNA of cosmid vector SuperCos1 (Wahl et al. (1987), Proceedings of the National Academy of Sciences, USA 84:2160–2164), obtained from Stratagene (La Jolla, USA, product description SuperCos1 Cosmid Vektor Kit, Code no. 251301), is cleaved with the restriction enzyme XbaI (Amersham Pharmacia, Freiburg, Germany, product description XbaI, Code no. 27-0948-02) and likewise dephosphorylated with shrimp alkaline phosphatase.

The cosmid DNA is then cleaved with the restriction enzyme BamHI (Amersham Pharmacia, Freiburg, Germany, product description BamHI, Code no. 27-0868-04). The cosmid DNA so treated is mixed with the treated ATCC13032 DNA, and the batch is treated with T4-DNA ligase (Amersham Pharmacia, Freiburg, Germany, product description T4-DNA ligase, Code no. 27-0870-04). The ligation mixture is then packed in phages with the aid of Gigapack II XL Packing Extracts (Stratagene, La Jolla, USA, product description Gigapack II XL Packing Extract, Code no. 200217).

For infection of *E. coli* strain NM554 (Raleigh et al. 1988, Nucleic Acid Res. 16:1563–1575), the cells are taken up in 10 mM $MgSO_4$ and mixed with an aliquot of the phage suspension. Infection and titration of the cosmid bank are carried out as described in Sambrook et al. (1989, Molecular Cloning: A Laboratory Manual, Cold Spring Harbor), the cells being plated out on LB agar (Lennox, 1955, Virology, 1:190)+100 mg/l ampicillin. After incubation overnight at 37° C., recombinant individual clones are selected.

EXAMPLE 2

Isolation and Sequencing of the citE Gene

The cosmid DNA of an individual colony is isolated using the Qiaprep Spin Miniprep Kit (Product No. 27106, Qiagen, Hilden, Germany) according to the manufacturer's instructions, and partially cleaved with the restriction enzyme Sau3AI (Amersham Pharmacia, Freiburg, Germany, product description Sau3AI, Product No. 27-0913-02). The DNA fragments are dephosphorylated with shrimp alkaline phosphatase (Roche Molecular Biochemicals, Mannheim, Germany, product description SAP, Product No. 1758250). After separation by gel electrophoresis, cosmid fragments having a size in the range from 1500 to 2000 bp are isolated using the QiaExII Gel Extraction Kit (Product No. 20021, Qiagen, Hilden, Germany).

The DNA of sequencing vector pZero-1, obtained from Invitrogen (Groningen, Netherlands, product description Zero Background Cloning Kit, Product No. K2500-01), is cleaved with the restriction enzyme BamHI (Amersham Pharmacia, Freiburg, Germany, product description BamHI, Product No. 27-0868-04). Ligation of the cosmid fragments into the sequencing vector pZero-1 is carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture is then electroporated into *E. coli* strain DH5αMCR (Grant, 1990, Proceedings of the National Academy of Sciences, U.S.A., 87:4645–4649) (Tauch et al. 1994, FEMS Microbiol. Letters, 123:343–347) and plated out on LB agar (Lennox, 1955, Virology, 1:190) with 50 mg/l Zeocin.

Plasmid preparation of the recombinant clones is carried out using the Biorobot 9600 (Product No. 900200, Qiagen, Hilden, Germany). Sequencing is effected by the dideoxy chain termination method of Sanger et al. (1977, Proceedings of the National Academies of Sciences, U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) is used. Separation by gel electrophoresis and analysis of the sequencing reaction is carried out in a "Rotiphorese NF Acrylamid/Bisacrylamid" gel (29:1) (Product No. A124.1, Roth, Karlsruhe, Germany) using the "ABI Prism 377" sequencing device from PE Applied Biosystems (Weiterstadt, Germany).

The resulting crude sequence data are then processed using the Staden program package (1986, Nucleic Acids Research, 14:217–231) Version 97-0. The individual sequences of the pZero1 derivatives are assembled to a coherent contig. The computer-assisted coding region analysis is prepared using the program XNIP (Staden, 1986, Nucleic Acids Research, 14:217–231).

The resulting nucleotide sequence is shown in SEQ ID No. 1. Analysis of the nucleotide sequence gives an open reading frame of 821 bp, which is designated the citE gene. The citE gene codes for a polypeptide of 273 amino acids.

EXAMPLE 3

Preparation of an Integration Vector for Integration Mutagenesis of the citE Gene Chromosomal DNA is isolated from strain ATCC 13032 by the method of Eikmanns et al. (Microbiology 140: 1817–1828 (1994)). On the basis of the sequence of the citE gene known from Example 2 for *C. glutamicum*, the following oligonucleotides are selected for the polymerase chain reaction (see also SEQ ID No. 3 and SEQ ID No. 4):

```
citE-int1
5' GAC GTG CTG AGA TCA TTC C 3' citE-int2
5' TAA GCC TCA TGG TGT CTC G 3'
```

The primers shown are synthesised by MWG Biotech (Ebersberg, Germany), and the PCR reaction is carried out according to the standard PCR method of Innis et al. (PCR protocols. A guide to methods and applications, 1990, Academic Press) using Taq polymerase from Boehringer Mannheim (Germany, product description Taq DNA Polymerase, Product No. 1 146 165). With the aid of the polymerase chain reaction, the primers permit the amplification of an internal fragment of the citE gene having a size of 450 bp. The product so amplified is tested by electrophoresis in a 0.8% agarose gel.

The amplified DNA fragment is ligated into vector pCR2.1-TOPO (Mead et al. (1991) Bio/Technology 9:657–663) using the TOPO TA Cloning Kit from Invitrogen Corporation (Carlsbad, Calif., USA; Catalog number K4500-01).

*E. coli* strain TOP10 is then electroporated with the ligation batch (Hanahan, in: DNA cloning. A practical approach. Vol. I. IRL-Press, Oxford, Washington D.C., USA, 1985). The selection of plasmid-carrying cells is carried out by plating out the transformation batch on LB agar (Sambrook et al., Molecular cloning: a laboratory manual. $2^{nd}$ ed. Cold Spring Harbor Laboratory Press, Cold Spring Harbor, N.Y., 1989), to which 50 mg/l kanamycin had been added. Plasmid DNA is isolated from a transformant with the aid of the QIAprep Spin Miniprep Kit from Qiagen, and is tested by restriction with the restriction enzyme EcoRI and subsequent agarose gel electrophoresis (0.8%). The plasmid is named pCR2.1citEint and is shown in FIG. 1.

EXAMPLE 4

Integration Mutagenesis of the citE Gene in Strain DSM 5715

Vector pCR2.1citEint mentioned in Example 3 is electroporated in *Corynebacterium glutamicum* DSM 5715 by the electroporation method of Tauch et al. (FEMS Microbiological Letters, 123:343–347 (1994)). Strain DSM 5715 is an AEC-resistant lysine producer, which is described in EP-B-04351342. Vector pCR2.1citEint is unable to replicate independently in DSM5715 and is retained in the cell only if it has integrated into the chromosome of DSM 5715. The selection of clones with pCR2.1citEint integrated into the chromosome is effected by plating out the electroporation batch on LB agar (Sambrook et al., Molecular cloning: a laboratory manual. 2$^{nd}$ ed. Cold Spring Harbor Laboratory Press, Cold Spring Harbor, N.Y.), to which 15 mg/l kanamycin had been added.

In order to demonstrate the integration, the citEint fragment is labelled by the method "The DIG System Users Guide for Filter Hybridization" from Boehringer Mannheim GmbH (Mannheim, Germany, 1993) using the Dig hybridization kit from Boehringer. Chromosomal DNA of a potential integrant is isolated by the method of Eikmanns et al. (Microbiology 140: 1817–1828 (1994)) and cleaved with each of the restriction enzymes EcoRI, BamHI and HindIII. The resulting fragments are separated by means of agarose gel electrophoresis and hybridized using the Dig hybridization kit from Boehringer at 68° C. Plasmid pCR2.1citEint mentioned in Example 3 has inserted into the chromosome of DSM5715 within the chromosomal citE gene. The strain is designated DSM5715::pCR2.1citEint.

EXAMPLE 5

Production of Lysine

The *C. glutamicum* strain DSM5715::pCR2.1citEint obtained in Example 4 is cultivated in a nutrient medium suitable for the production of lysine, and the lysine content in the culture supernatant is determined.

To that end, the strain is first incubated for 24 hours at 33° C. on agar plate with the corresponding antibiotic (brain-heart agar with kanamycin (25 mg/l). Starting from that agar plate culture, a pre-culture is inoculated (10 ml of medium in 100 ml Erlenmeyer flasks). CgIII complete medium is used as the medium for the pre-culture.

| Cg III medium | |
|---|---|
| NaCl | 2.5 g/l |
| Bacto-peptone | 10 g/l |
| Bacto-yeast extract | 10 g/l |
| Glucose (autoclaved separately) | 2% (w/v) |

The pH value is adjusted to pH 7.4

Kanamycin (25 mg/l) is added thereto. The pre-culture is incubated for 48 hours at 33° C. at 240 rpm on a shaker. A main culture is inoculated from that pre-culture, so that the initial OD (660 nm) of the main culture is 0.1 OD. MM medium is used for the main culture.

| MM medium | |
|---|---|
| CSL (corn steep liquor) | 5 g/l |
| MOPS (morpholinopropane sulfonic acid) | 20 g/l |
| Glucose (autoclaved separately) | 50 g/l |
| Salts: | |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterilised by filtration) | 0.3 mg/l |
| Thiamin * HCl (sterilised by filtration) | 0.2 mg/l |
| Leucine (sterilised by filtration) | 0.1 g/l |
| $CaCO_3$ | 25 g/l |

CSL, MOPS and the salt solution are adjusted to pH 7 with ammonia water and autoclaved. The sterile substrate and vitamin solutions are then added, as well as the dry autoclaved $CaCO_3$.

Cultivation is carried out in a volume of 10 ml in a 100 ml Erlenmeyer flask with baffles. Kanamycin (25 mg/l) is added. Cultivation is carried out at 33° C. and 80% atmospheric humidity.

After 72 hours, the OD is determined at a measuring wavelength of 660 nm using a Biomek 1000 (Beckmann Instruments GmbH, Munich). The amount of lysine that has formed is determined using an amino acid analyzer from Eppendorf-BioTronik (Hamburg, Germany) by ion-exchange chromatography and post-column derivatization with ninhydrin detection.

The result of the test is shown in Table 1.

TABLE 1

| Strain | OD(660) | Lysine HCl g/l |
|---|---|---|
| DSM5715 | 8.2 | 13.7 |
| DSM5715::pCR2.1citEint | 8.4 | 15.9 |

The following Figure is attached:
FIG. 1 Map of plasmid pCR2.1cit Eint.
The abbreviations and names used have the following meanings.
kmR: kanamycin resistance gene
EcoRI: EcoRI restriction enzyme cleavage site
hindIII: hindIII restriction enzyme cleavage site
BamHI: BamHI restriction enzyme cleavage site
CitEint: internal fragment of the citE gene
ColE1: origin of replication of plasmid ColE1

The invention claimed is:

1. A fermentation process suitable for the preparation of an L-amino acid, wherein the following steps are carried out:
   (a) fermentation of a coryneform bacterium strain in a fermentation broth for producing the desired L-amino acid, wherein the endogenous citrate lyase E (citE) gene as set forth in SEQ ID No: 1 is inactivated by one or more methods of mutagenesis selected from the group consisting of deletion, insertional mutagenesis due to homologous recombination, and transition or transversion mutagenesis with incorporation of a nonsense mutation in the citE gene, and
   (b) concentration of the fermentation broth to eliminate water and increase the concentration of said L-amino acid in the broth and coryneform bacterium, and
   (c) isolation of the L-amino acid.

2. The process according to claim 1 wherein the coryneform bacterium contains one or more *C. glutamicum* genes selected from the group consisting of the gene dapA coding for dihydropicolinate synthase, the gene gap coding for glyceraldehyde 3-phosphate dehydrogenase, the gene tpi coding for triose phosphate isomerase, the gene pgk coding for 3-phosphoglycerate kinase, the gene zwf coding for glucose-6-phosphate dehydrogenase the gene pyc coding for pyruvate carboxylase, the gene mqo coding for malate quinone oxidoreductase, the gene lysE coding for lysine export, and the gene zwa1 coding for the Zwa1 protein wherein said gene or genes are overexpressed by increasing the copy number or placing under a strong promoter during fermentation of said L-amino acid.

3. The process according to claim 1, wherein the coryneform bacterium is *C. glutamicum* and wherein one or more *C. glutamicum* genes selected from the group the gene pck coding for phosphoenol pyruvate carboxykinase, the gene pgi coding for glucose-6-phosphate isornerase, the gene poxB coding for pyruvate oxidase, the gene zwa2 coding for the Zwa2 protein, the gene hom coding for homoserine dehydrogenase, the gene thrB coding for homoserine kinase, and the gene panD coding for aspartate decarboxylase are inactivated by one or more methods of mutagenesis selected from the group consisting of deletion, insertional mutagenesis due to homologous recombination, and transition or transversion mutagenesis with incorporation of a non-sense mutation in said gene or genes.

4. The process of claim 1, wherein the constituents of the fermentation broth and the biomass in its entirety or portions thereof are isolate as a solid product together with said L-amino acids.

5. The process according to claim 1, wherein L-amino acids are produced by fermenting coryneform bacteria wherein the endogenous citE gene is inactivated by homologous recombination using vector pCR2.1citEint deposited in *E. coli* under DSM 13981.

6. The process according to claim 1, wherein L-lysine is produced by fermenting coryneform bacteria wherein the endogenous citE gene is inactivated by homologous recombination using vector pCR2.1citEint deposited in *E. coil* under DSM 13981.

* * * * *

SEQUENCE LISTING

```
<160> NUMBER OF SEQ ID NOS: 4

<210> SEQ ID NO 1
<211> LENGTH: 1964
<212> TYPE: DNA
<213> ORGANISM: Corynebacterium glutamicum
<220> FEATURE:
<221> NAME/KEY: CDS
```

-continued

```
<222> LOCATION: (602)..(1420)

<400> SEQUENCE: 1
ggcgctgtgg agatcctgag ccagaagaag aacatccgta ttcttcaggc tgaagcacct      60
gtgcgtaagg gctttgagtc ccgtgagatc tccggcggtc tgcttgttca ggaacgcgac     120
ttgatccacg ctgagggcga caactccgca aactggactc ttgctgccgg ctctgctgtt     180
tctcctgagg ttctgaagga cctggagttc gcgtggactg cagttcgttc cgtgaagtcc     240
aacgcaattc tgttggctaa gaacggcgct accgttggcg ttggcatggg acaggtcaac     300
cgcgttgact ctgctcgctt ggctgtcgac cgtgcaggtg cagagcgcgc taccggttcc     360
gttgctgctt ccgatgcgtt cttcccattc gctgacggct tgaggttct cgctgaggct      420 ggcatcactg ctgttgtgca gcctggtgga tccattcgcg acaacgaggt cattgaggca     480
gccaacaagg ctggcgtgac catgtacctg actggtgcgc gacacttcgc tcactaaagt     540
ttttaaagat ttcgcttgaa ggcagaccat aaggtctgcc ttttcgcgta ttaatgagta     600 c atg tct gaa ctt att tgt gga cca gct att ctc ttc gca cca gct gga    649
  Met Ser Glu Leu Ile Cys Gly Pro Ala Ile Leu Phe Ala Pro Ala Gly
  1               5                   10                  15 cgt gct gag atc att cca aaa gca gca tcg aag gcc gat atg gtc atc    697
Arg Ala Glu Ile Ile Pro Lys Ala Ala Ser Lys Ala Asp Met Val Ile
             20                  25                  30 att gat ttg gaa gat ggg gca ggg gag gta gac cgt gag gtc gcc tac    745
Ile Asp Leu Glu Asp Gly Ala Gly Glu Val Asp Arg Glu Val Ala Tyr
         35                  40                  45 agg aac att aga gaa tcg ggg ttg gat cct aaa cga acc att gtg aga    793
Arg Asn Ile Arg Glu Ser Gly Leu Asp Pro Lys Arg Thr Ile Val Arg
     50                  55                  60 acc gta ggg ccg agc gat cca cac ttt ttg gct gac gtg gag atg gtg    841
Thr Val Gly Pro Ser Asp Pro His Phe Leu Ala Asp Val Glu Met Val
 65                  70                  75                  80 aag tcc acg gat ttc aca ctt gtt atg gtt cct aaa ctt ctt ggc agc    889
Lys Ser Thr Asp Phe Thr Leu Val Met Val Pro Lys Leu Leu Gly Ser
                 85                  90                  95 gtg cct gag gaa tta gat ggc ctc aac att atc gcc atg att gaa acc    937
Val Pro Glu Glu Leu Asp Gly Leu Asn Ile Ile Ala Met Ile Glu Thr
            100                 105                 110 cct cag gct gca acc agc att cct cag att gct gcg gac cct aaa gtc    985
Pro Gln Ala Ala Thr Ser Ile Pro Gln Ile Ala Ala Asp Pro Lys Val
        115                 120                 125 gtt gga atg ttc tgg ggc gcg gag gat ctc aca cac ctc ttg gga ggc   1033
Val Gly Met Phe Trp Gly Ala Glu Asp Leu Thr His Leu Leu Gly Gly
    130                 135                 140 act cat tct agg ttc ttg ggt gat gag tcc aat gaa ggc tcc tac cga   1081
Thr His Ser Arg Phe Leu Gly Asp Glu Ser Asn Glu Gly Ser Tyr Arg
145                 150                 155                 160 gac acc atg agg ctt aca cgc gcc ctg atg cac ctc cac gcg gcg gcg   1129
Asp Thr Met Arg Leu Thr Arg Ala Leu Met His Leu His Ala Ala Ala
                165                 170                 175 aat ggg aag ttc acc att gat gcc atc cat gcg gat ttc cac gat gaa   1177
Asn Gly Lys Phe Thr Ile Asp Ala Ile His Ala Asp Phe His Asp Glu
            180                 185                 190 gag ggc ctc tat tta gaa gcg gtc gat gct gcg cgg act ggt ttc gct   1225
Glu Gly Leu Tyr Leu Glu Ala Val Asp Ala Ala Arg Thr Gly Phe Ala
        195                 200                 205 ggc acc gca tgc att cac ccc aag cag atc gag att gtt cgg aga gcc   1273
Gly Thr Ala Cys Ile His Pro Lys Gln Ile Glu Ile Val Arg Arg Ala
    210                 215                 220
```

```
tat cgg cca gag gct aac cag ttg gag tgg gcg aag aaa gtg gtg gag    1321
Tyr Arg Pro Glu Ala Asn Gln Leu Glu Trp Ala Lys Lys Val Val Glu
225                 230                 235                 240 gaa gca gaa aac cat cca ggt gcg ttc aaa ctg gat ggt cag atg att    1369
Glu Ala Glu Asn His Pro Gly Ala Phe Lys Leu Asp Gly Gln Met Ile
                245                 250                 255 gat gct ccg ttg att tcg cag gcg cgg atg gtt att tcg cgt cag cct    1417
Asp Ala Pro Leu Ile Ser Gln Ala Arg Met Val Ile Ser Arg Gln Pro
            260                 265                 270 gct tgattagttc aagcgttttt tcgacccggt cggcgggcag cggcgcgccg         1470
Ala aggacggcga gggaggcgtc ggcaagcata attgcggtct ccgggaggct gtctgcggaa  1530
agcgggcttg gaatcttgcc gtcgttgcga cgcatttcga tcaccgacat ggtgatgtgg  1590
aaggggagtt ctgcgcgggg gtcgtcaccg acgatttcgg tggcgaggtc gcggaagacg  1650
ttggtgaggc cttcgcgctg gctgtggtac tcggcgaact cttcagaacc aacgatgggg  1710
agttggtaca ggcgaccgac gttccacttg gtggacagca gcagacgcac ttcggaggca  1770
acgattgccc agaggcgcat ctcaggtccg cgtccaggg tgcttaagtc ttcggcgagc   1830
acagtggacg gctcgacagt agatttcagc agggtgagga agatttccgt cttggacggg  1890
aagtgataat acagcgaggc ttggcggatt cccacggcat cagcgatttg atgcgtggag  1950
gttgttgcga agcc                                                    1964

<210> SEQ ID NO 2
<211> LENGTH: 273
<212> TYPE: PRT
<213> ORGANISM: Corynebacterium glutamicum

<400> SEQUENCE: 2

Met Ser Glu Leu Ile Cys Gly Pro Ala Ile Leu Phe Ala Pro Ala Gly
1               5                   10                  15

Arg Ala Glu Ile Ile Pro Lys Ala Ala Ser Lys Ala Asp Met Val Ile
                20                  25                  30

Ile Asp Leu Glu Asp Gly Ala Gly Glu Val Asp Arg Gly Val Ala Tyr
            35                  40                  45

Arg Asn Ile Arg Glu Ser Gly Leu Asp Pro Lys Arg Thr Ile Val Arg
        50                  55                  60

Thr Val Gly Pro Ser Asp Pro His Phe Leu Ala Asp Val Glu Met Val
65                  70                  75                  80

Lys Ser Thr Asp Phe Thr Leu Val Met Val Pro Lys Leu Leu Gly Ser
                85                  90                  95

Val Pro Glu Glu Leu Asp Gly Leu Asn Ile Ile Ala Met Ile Glu Thr
                100                 105                 110

Pro Gln Ala Ala Thr Ser Ile Pro Gln Ile Ala Ala Asp Pro Lys Val
            115                 120                 125

Val Gly Met Phe Trp Gly Ala Glu Asp Leu Thr His Leu Leu Gly Gly
        130                 135                 140

Thr His Ser Arg Phe Leu Gly Asp Glu Ser Asn Glu Gly Ser Tyr Arg
145                 150                 155                 160

Asp Thr Met Arg Leu Thr Arg Ala Leu Met His Leu His Ala Ala Ala
                165                 170                 175

Asn Gly Lys Phe Thr Ile Asp Ala Ile His Ala Asp Phe His Asp Glu
            180                 185                 190

Glu Gly Leu Tyr Leu Glu Ala Val Asp Ala Ala Arg Thr Gly Phe Ala
```

```
                    195                 200                 205
Gly Thr Ala Cys Ile His Pro Lys Gln Ile Glu Ile Val Arg Arg Ala
        210                 215                 220
Tyr Arg Pro Glu Ala Asn Gln Leu Glu Trp Ala Lys Lys Val Val Glu
225                 230                 235                 240
Glu Ala Glu Asn His Pro Gly Ala Phe Lys Leu Asp Gly Gln Met Ile
                245                 250                 255
Asp Ala Pro Leu Ile Ser Gln Ala Arg Met Val Ile Ser Arg Gln Pro
            260                 265                 270
Ala

<210> SEQ ID NO 3
<211> LENGTH: 19
<212> TYPE: DNA
<213> ORGANISM: PCR primer

<400> SEQUENCE: 3
gacgtgctga gatcattcc                                                    19

<210> SEQ ID NO 4
<211> LENGTH: 19
<212> TYPE: DNA
<213> ORGANISM: PCR primer

<400> SEQUENCE: 4
taagcctcat ggtgtctcg                                                    19
```